United States Patent [19]

Fleischle

[11] Plant 4,523

[45] Apr. 22, 1980

[54] DISTINCT VARIETY OF STREPTOCARPUS NAMED ILSA

[75] Inventor: Gerhard Fleischle, Vaihingen, Fed. Rep. of Germany

[73] Assignee: Oglevee Associates, Inc., Connellsville, Pa.

[21] Appl. No.: 958,833

[22] Filed: Nov. 8, 1978

[30] Foreign Application Priority Data

Jul. 7, 1978 [DE] Fed. Rep. of Germany ..... S.T.C.1

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Webb, Burden, Robinson & Webb

[57] ABSTRACT

A new variety of Streptocarpus plant is characterized by its pure white flower having veined royal purple color. It has large flowers, long permanence and is generally nonfertile.

1 Drawing Figure

BACKGROUND OF THE NEW PLANT

The present invention comprises the new and distinct cultivar of *Streptocarpus x hybridus* known by the varietal name Ilsa, formerly named Juwel. The new cultivar is an irradiated sport of a Streptocarpus known by the varietal name of Laura.

The major difference when compared with Laura is in color, Laura having a blue flower. In addition, the new cultivar has larger and more persistant blooms and is nonfertile as compared to Laura.

The new cultivar was discovered in 1977 in Vaihingen, Federal Republic of Germany; was first asexually reproduced by cuttings in Vaihingen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of nine weeks. Response time is defined as the period of time from a plantlet which is a well rooted young plant in a five centimeter pot to a flowering plant in a ten centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on eight week plants blossomed under natural light in a greenhouse and color readings were taken indoors under 100 foot candles of cool white fluorescent light. Color references are primarily to the R.H.S. color chart of the Royal Horticultural Society of London. Some color reference is to Exotica III and such reference is duly noted.

Botanical classification: Gesneriaceae (family); *Streptocarpus x hybridus* (genus x species).

Flower:

*Fully expanded.*—Seven centimeters.

*Borne.*—In clusters of one to six flowers per flower stalk above the foliage. Flower stalks arise from mid-rib of each leaf.

*Stems.*—Single, long and pubescent.

*Form.*—Funnel formed in an umbel.

*Permanence.*—Long lasting 21 to 25 days.

Color:

*Front of petals.*—Pure white.

*Throat.*—Pure white with a plurality of stripes, Fan 2 Purple Violet Group 82-B extending into the center of the petals.

*Base of petals.*—Pure white.

*Reverse of petals.*—Pure white.

*Tonality from a distance.*—White and veined royal purple (Exotica III).

*Discoloration.*—Insignificant.

Petals:

*Texture.*—Velvet.

*Appearance.*—Individually lobed, ruffled and irregular serration for margin.

*Arrangement.*—Regularly united into an elliptical form.

*Persistance.*—Lives for 21 to 25 days and remains on plant in dry form until picked.

*Fragrance.*—None.

Reproductive organs:

*Anthers.*—Two per flower and interconnected.

*Filament.*—Two and one-half inch centimeters initiating from the base of the petal and extending to the anther. In addition, two undeveloped stamens are present.

*Pollen.*—Generally nonfertile.

*Style.*—Extends from tip of ovary one centimeter and terminates in a flattened stigma.

*Ovaries.*—Long and narrow, one and one-half millimeters in diameter and one and one-half centimeters long.

Plant:

*Form.*—Leaves rosulete from a crown at the soil line.

*Growth.*—A spreading, free flowing habit with leaf bases being acute.

*Height from soil line.*—20 to 30 centimeters.

*Spread.*—35 to 40 centimeters.

Foliage:

*Top side.*—Fan 3 Green Group 137-B.

*Size.*—15 to 30 centimeters in length and 6 to 9 centimeters wide at the widest point.

*Quantity.*—10 to 15 leaves.

*Shape.*—Oblanceolete.

*Ribs and veins.*—Pinnate.

*Rib and vein color.*—Fan 3 Green Group 138-B.

*Margin.*—Crenate serrations.

*Underside.*—Fan 4 Greyed Green Group 193-A.

*Stipules.*—None.

I claim:

1. A new and distinct variety of Streptocarpus substantially as herein shown and described.

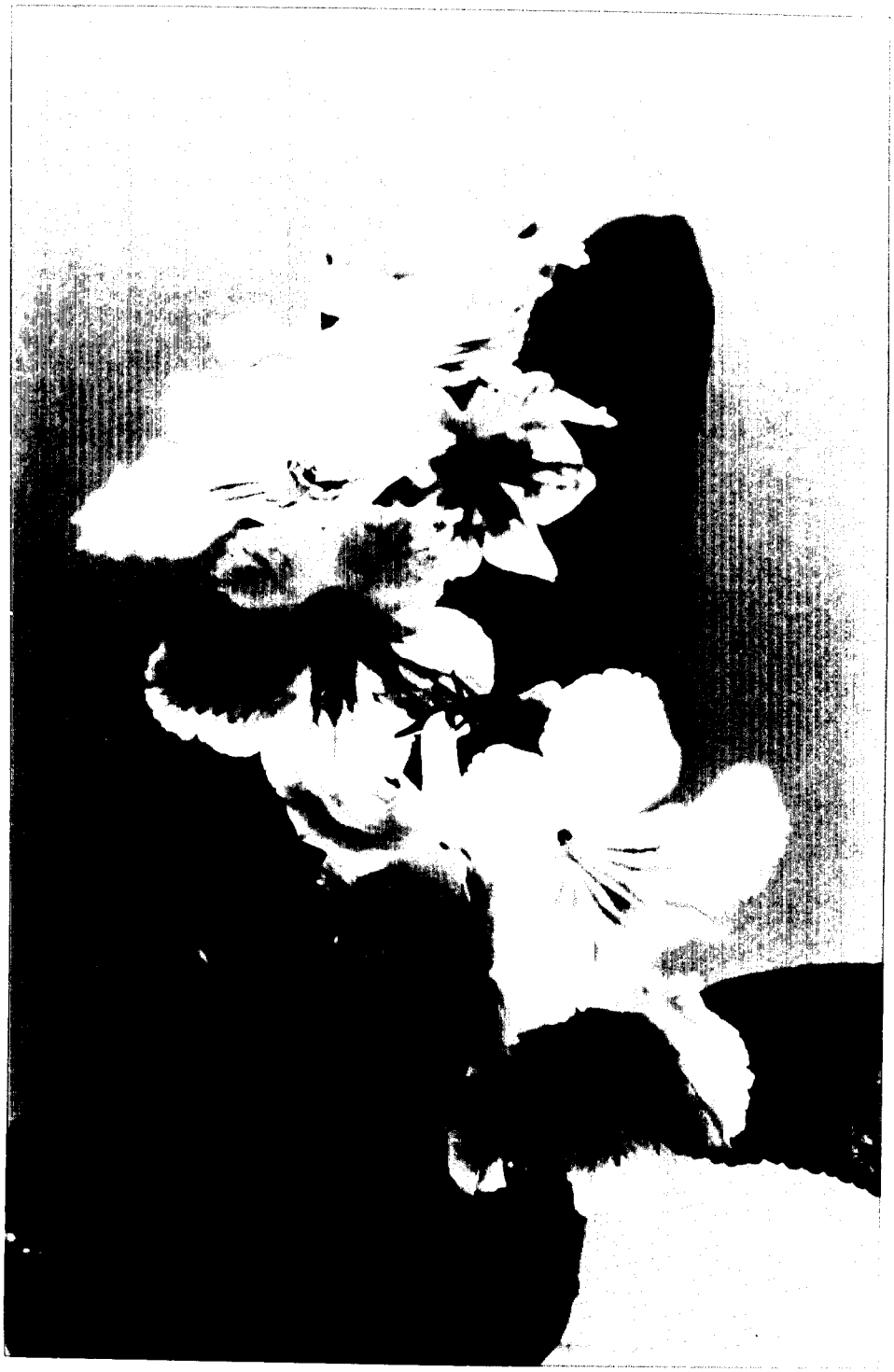

* * * * *